US009956434B2

(12) United States Patent
Cassin et al.

(10) Patent No.: US 9,956,434 B2
(45) Date of Patent: May 1, 2018

(54) COSMETIC COMPOSITION COMPRISING SILICA AEROGEL PARTICLES AND SILICONE OILS

(75) Inventors: Guillaume Cassin, Villebon sur Yvette (FR); Sylvie Poret Fristot, Rungis (FR)

(73) Assignee: L'Oreal, Paris (FR)

(*) Notice: Subject to any disclaimer, the term of this patent is extended or adjusted under 35 U.S.C. 154(b) by 416 days.

(21) Appl. No.: 13/995,773

(22) PCT Filed: Dec. 19, 2011

(86) PCT No.: PCT/EP2011/073187
§ 371 (c)(1),
(2), (4) Date: Aug. 28, 2013

(87) PCT Pub. No.: WO2012/084780
PCT Pub. Date: Jun. 28, 2012

(65) Prior Publication Data
US 2013/0337026 A1 Dec. 19, 2013

Related U.S. Application Data

(60) Provisional application No. 61/436,277, filed on Jan. 26, 2011.

(30) Foreign Application Priority Data

Dec. 21, 2010 (FR) ...................... 10 60893

(51) Int. Cl.
A61K 8/25 (2006.01)
A61Q 19/00 (2006.01)
A61K 8/58 (2006.01)
A61K 8/02 (2006.01)
A61K 8/891 (2006.01)
A61Q 1/04 (2006.01)
A61Q 5/00 (2006.01)

(52) U.S. Cl.
CPC .......... *A61Q 19/007* (2013.01); *A61K 8/0279* (2013.01); *A61K 8/25* (2013.01); *A61K 8/585* (2013.01); *A61K 8/891* (2013.01); *A61Q 19/008* (2013.01); *A61Q 1/04* (2013.01); *A61Q 5/00* (2013.01)

(58) Field of Classification Search
CPC .......... A61Q 19/007; A61Q 1/04; A61Q 5/00; A61Q 19/008; A61K 8/0279; A61K 8/25; A61K 8/891; A61K 8/585
USPC ...................................................... 424/401
See application file for complete search history.

(56) References Cited

U.S. PATENT DOCUMENTS

| 5,800,816 | A | 9/1998 | Brieva et al. |
| 5,911,974 | A | 6/1999 | Brieva et al. |
| 5,965,112 | A | 10/1999 | Brieva et al. |
| 5,985,298 | A | 11/1999 | Brieva et al. |
| 6,464,964 | B1 | 10/2002 | Brieva et al. |
| 2003/0007987 | A1 | 1/2003 | Brieva et al. |
| 2003/0147931 | A1 | 8/2003 | Brieva et al. |
| 2003/0199660 | A1* | 10/2003 | Sakuta ............... A61K 8/89 528/25 |
| 2004/0175345 | A1 | 9/2004 | Brieva et al. |
| 2005/0255134 | A1 | 11/2005 | Hasenzahl et al. |
| 2006/0088562 | A1 | 4/2006 | Brieva et al. |
| 2007/0092468 | A1 | 4/2007 | Brieva et al. |
| 2009/0068255 | A1* | 3/2009 | Yu ............... A61K 8/0212 424/450 |
| 2009/0247648 | A1 | 10/2009 | Zhao |
| 2012/0065163 | A1 | 3/2012 | Zhao |

FOREIGN PATENT DOCUMENTS

| WO | WO 03/022229 A1 | 3/2003 |
| WO | WO 2005/058256 A1 | 6/2005 |
| WO | WO 2009/059869 A2 | 5/2009 |
| WO | WO 2009/120602 A1 | 10/2009 |

OTHER PUBLICATIONS

Dynamic (Absolute) and Kinematic Viscosity of Water: retrieved from internet: http://www.engineeringtoolbox.com/water-dynamic-kinematic-viscosity-d_596.html. Retrieved on Feb. 23, 3015.*
Phenylated silicone fluid: retrieved from internet: https://www.shinetsusilicone-global.com/products/personalcare/pdf/KF/KF-54.pdf. Retrieved on Aug. 18, 2016.*
Phenyl Trimethicone: retrieved from internet: www.caldic-techniek.nl/.../TDS%20CP%2020%20Phenyl%20Trimethicone.pdf. Retrieved on Aug. 18, 2016.*
Low Viscosity Caprylyl Methicone Silicone Oil for Personal Care: retrieved from internet: http://m.silicone-oils.com/sale-7619266-low-viscosity-caprylyl-methicone-silicone-oil-for-personal-care.html. Retrieved on Aug. 18, 2016.*
International Search Report issued Nov. 29, 2012 in Application No. PCT/EP2011/073187.

(Continued)

Primary Examiner — Hong Yu
(74) Attorney, Agent, or Firm — Oblon, McClelland, Maier & Neustadt, L.L.P.

(57) ABSTRACT

The present invention relates to a composition comprising a mixture: of hydrophobic silica aerogel particles having a specific surface area per unit of mass ($S_M$) ranging from 500 to 1500 m²/g and a size expressed as the volume-average diameter (D[0.5]) ranging from 1 to 1500 µm, and of at least one first linear silicone oil having a viscosity greater than 50 mm²/s and of at least second and third linear silicone oils having a viscosity less than or equal to 50 mm²/s. The present invention also relates to a cosmetic composition comprising a mixture: of hydrophobic silica aerogel particles having a specific surface area per unit of mass ($S_M$) ranging from 500 to 1500 m²/g and a size expressed as the volume-average diameter (D[0.5]) ranging from 1 to 1500 µm, and of at least one first linear silicone oil having a viscosity less than 10 mm²/s and of at least one second linear silicone oil having a viscosity greater than or equal to 10 mm²/s. The mixture of silica aerogel particles and linear silicone oils makes it possible to obtain compositions that are comfortable and soft on application, having mattifying and soft-focus properties.

24 Claims, No Drawings

(56) References Cited

OTHER PUBLICATIONS

"Product information: Dow Corning VM-2270 Aerogel Fine particles", Dow Corning, Retrieved from the Internet: URL http://www2.dowcorning.com/DataFiles/090007c88020e235.pdf, Apr. 1, 2009, XP002650585, 4 pages.

"Silica Silylate Aerogel for Cosmetic Applications", IP.com Journal, Jan. 30, 2006, XP013112635, 3 pages.

Database GNPD [Online] Mintel, "Superfit Makeup", Database Accession No. 1005357, XP002650586, Nov. 2008, 4 pages.

Office Action issued Oct. 2, 2014 in Russia Patent Application No. 2013129538 (with English language translation).

\* cited by examiner

COSMETIC COMPOSITION COMPRISING SILICA AEROGEL PARTICLES AND SILICONE OILS

The invention relates to a cosmetic composition for keratin materials, especially the skin and the lips, the hair and the nails. The invention also relates to a cosmetic method for treating keratin materials using said composition.

In the field of cosmetic skin care compositions, it is known practice to use soft-focus inorganic or organic fillers that absorb sebum and perspiration, in order to mattify the skin and/or optically smooth the microrelief and camouflage the imperfections of the skin.

However, the use of these fillers is generally accompanied by a dry, rough feel and a lack of comfort that is unacceptable for the user.

Silicone elastomers are also widely used as a mattifying agent because they make it possible to obtain a soft feel on the skin, but they must be used at a relatively high content in order to have the mattifying effect, which constitutes a restraint in the choice of the texture and in the cost of the formulation.

However, there is still a need for cosmetic compositions that are mattifying and/or that make it possible to mask skin imperfections, which have good cosmetic properties, in particular which are soft on application and are less restrictive in terms of cost.

The Applicant has discovered that this need can be met by combining in a composition, hydrophobic silica aerogel particles and a specific mixture of silicone oils.

More specifically, one subject of the present invention is a cosmetic composition comprising a mixture:
  of hydrophobic silica aerogel particles having a specific surface area per unit of mass ($S_M$) ranging from 500 to 1500 $m^2/g$ and a size expressed as the volume-average diameter (D[0.5]) ranging from 1 to 1500 µm, and
  of at least one first linear silicone oil having a viscosity greater than 50 $mm^2/s$ and of at least second and third linear silicone oils each having a viscosity less than or equal to 50 $mm^2/s$.

Another subject of the present invention is a cosmetic composition comprising a mixture:
  of hydrophobic silica aerogel particles having a specific surface area per unit of mass ($S_M$) ranging from 500 to 1500 $m^2/g$ and a size expressed as the volume-average diameter (D[0.5]) ranging from 1 to 1500 µm, and
  of at least one first linear silicone oil having a viscosity less than 10 $mm^2/s$ and of at least one second linear silicone oil having a viscosity greater than or equal to 10 $mm^2/s$.

The mixture of silica aerogel particles and linear silicone oils makes it possible to obtain compositions that are comfortable and soft on application, having mattifying and soft-focus properties. It may be used to completely or partially replace the silicone elastomers conventionally used to obtain these properties.

The mixture of hydrophobic silica aerogel particles and of silicone oils is advantageously in the form of a gel that does not flow under its own weight.

Another subject of the present invention is a mixture:
  of hydrophobic silica aerogel particles having a specific surface area per unit of mass ($S_M$) ranging from 500 to 1500 $m^2/g$ and a size expressed as the volume-average diameter (D[0.5]) ranging from 1 to 1500 µm, and
  of at least one first linear silicone oil having a viscosity greater than 50 $mm^2/s$ and of at least second and third linear silicone oil each having a viscosity less than or equal to 50 $mm^2/s$.

Another subject of the present invention is a mixture:
  of hydrophobic silica aerogel particles having a specific surface area per unit of mass ($S_M$) ranging from 500 to 1500 $m^2/g$ and a size expressed as the volume-average diameter (D[0.5]) ranging from 1 to 1500 µm, and
  of at least one first linear silicone oil having a viscosity less than 10 $mm^2/s$ and of at least one second linear silicone oil having a viscosity greater than or equal to 10 $mm^2/s$.

Another subject of the present invention is a cosmetic method for making up and/or caring for keratin materials comprising a step of applying a composition as defined above to said materials.

In what follows, the expression "at least one" is equivalent to "one or more" and, unless otherwise indicated, the limits of a range of values are included in that range.

Hydrophobic Silica Aerogels:

Silica aerogels are porous materials obtained by replacing (by drying) the liquid component of a silica gel with air.

They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles used in the present invention have a specific surface area per unit of mass ($S_M$) ranging from 500 to 1500 $m^2/g$, preferably from 600 to 1200 $m^2/g$ and better still from 600 to 800 $m^2/g$, and a size expressed as the volume-average diameter (D[0.5]) ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles used in the present invention have a size expressed as the volume-average diameter (D[0.5]) ranging from 1 to 30 µm, preferably from 5 to 25 µm, better still from 5 to 20 µm and even better still from 5 to 15 µm.

The specific surface area per unit of mass may be determined via the BET (Brunauer-Emmett-Teller) nitrogen absorption method described in the *Journal of the American Chemical Society*, vol. 60, page 309, February 1938 and corresponding to the international standard ISO 5794/1 (appendix D). The BET specific surface area corresponds to the total specific surface area of the particles under consideration.

The sizes of the silica aerogel particles may be measured by static light scattering using a commercial particle size analyser such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

According to one advantageous embodiment, the hydrophobic silica aerogel particles used in the present invention have a specific surface area per unit of mass ($S_M$) ranging from 600 to 800 m²/g and a size expressed as the volume-average diameter (D[0.5]) ranging from 5 to 20 μm and even better still from 5 to 15 μm.

The silica aerogel particles used in the present invention may advantageously have a tapped density ( ) ranging from 0.04 g/cm³ to 0.10 g/cm³ and preferably from 0.05 g/cm³ to 0.08 g/cm³.

In the context of the present invention, this density, known as the tapped density, may be assessed according to the following protocol:

40 g of powder are poured into a measuring cylinder; the measuring cylinder is then placed on a Stay 2003 machine from Stampf Volumeter; the measuring cylinder is then subjected to a series of 2500 tapping actions (this operation is repeated until the difference in volume between two consecutive tests is less than 2%); the final volume Vf of tapped powder is then measured directly on the measuring cylinder. The tapped density is determined by the ratio m/Vf, in this instance 40/Vf (Vf being expressed in cm³ and m in g).

According to one embodiment, the hydrophobic silica aerogel particles used in the present invention have a specific surface area per unit of volume $S_V$ ranging from 5 to 60 m²/cm³, preferably from 10 to 50 m²/cm³ and better still from 15 to 40 m²/cm³.

The specific surface area per unit of volume is given by the relationship: $S_V = S_M \times \rho$ where $\rho$ is the tapped density expressed in g/cm³ and $S_M$ is the specific surface area per unit of mass expressed in m²/g, as defined above.

Preferably, the hydrophobic silica aerogel particles according to the invention have an oil absorption capacity, measured at the wet point, ranging from 5 to 18 ml/g, preferably from 6 to 15 ml/g and better still from 8 to 12 ml/g.

The absorption capacity measured at the wet point, noted Wp, corresponds to the amount of oil that needs to be added to 100 g of particles in order to obtain a homogeneous paste.

It is measured according to the wet point method or the method for determining the oil uptake of a powder described in standard NF T 30-022. It corresponds to the amount of oil adsorbed onto the available surface of the powder and/or absorbed by the powder by measuring the wet point, described below:

An amount, m=2 g, of powder is placed on a glass plate, and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The aerogels used according to the present invention are hydrophobic silica aerogels, preferably of silyl silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogels particles that have been surface-modified by silylation, reference may be made to document U.S. Pat. No. 7,470,725.

Use will be made in particular of hydrophobic silica aerogels particles surface-modified with trimethylsilyl groups.

As hydrophobic silica aerogels that may be used in the invention, examples that may be mentioned include the aerogel sold under the name VM-2260 (INCI name: Silica silylate), by the company Dow Corning, the particles of which have an average size of about 1000 microns and a specific surface area per unit of mass ranging from 600 to 800 m²/g.

Mention may also be made of the aerogels sold by the company Cabot under the references AEROGEL TLD 201, AEROGEL OGD 201, AEROGEL TLD 203, ENOVA® AEROGEL MT 1100, ENOVA AEROGEL MT 1200.

Use will be made more particularly of the aerogel sold under the name VM-2270 (INCI name: Silica silylate), by the company Dow Corning, the particles of which have an average size ranging from 5-15 microns and a specific surface area per unit of mass ranging from 600 to 800 m²/g.

The hydrophobic silica aerogel particles may represent from 0.5% to 30% by weight, preferably from 1% to 20% by weight, better still from 2% to 15% by weight, more preferably from 5% to 10% by weight, even better still from 6% to 8% by weight of the mixture (linear silicone oils and silica aerogels) according to the invention.

The hydrophobic silica aerogel particles may be present in the composition according to the invention in a content ranging from 0.05% to 15% by weight, preferably from 0.1% to 10% by weight, better still from 0.5% to 5% by weight and more preferably from 0.5% to 2% by weight relative to the total weight of the composition.

Silicone Oils:

The composition according to the invention comprises at least one first linear silicone oil having a viscosity greater than 50 mm²/s, preferably greater than or equal to 100 mm²/s, better still greater than or equal to 200 mm²/s, even better still greater than or equal to 300 mm²/s, and which may range up to 500 mm²/s.

It also comprises at least second and third linear silicone oils each having a viscosity less than or equal to 50 mm²/s, preferably less than or equal to 30 mm²/s, better still less than or equal to 20 mm²/s, even better still less than or equal to 15 mm²/s and which may be greater than 1 mm²/s.

The viscosity of the silicone oil may be measured according to standard ASTM D-445.

The term "oil" means a fatty substance that is liquid at room temperature (25° C.).

The term "silicone oil" means an oil comprising at least one silicon atom, especially comprising Si—O groups.

The linear silicone oils are preferably polyorganosiloxanes comprising alkylsiloxane repeat units, the alkyl groups preferably comprising from 1 to 6 carbon atoms and preferably being unsubstituted.

In particular, the linear silicone oils are chosen from polydimethylsiloxanes (INCI name: dimethicone), preferably of formula:

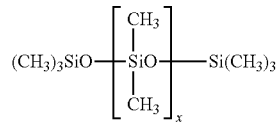

in which x is an integer chosen so as to have a fluid compound.

According to one embodiment, the first linear silicone oil is present in the mixture of linear silicone oils in a content less than or equal to 20% by weight relative to the total weight of the mixture of linear silicone oils (first, second and third linear silicone oils), preferably less than or equal to 10% by weight, better still less than or equal to 5% by weight. It may represent from 0.5% to 20% by weight, better still from 1% to 15% by weight, even better still from 1% to 10% by weight and more preferably from 1% to 5% by weight relative to the total weight of the mixture of linear silicone oils.

The expression "mixture of linear silicone oils" is understood to mean the mixture of first, second and third linear silicone oils.

According to one embodiment, each second and third linear silicone oil is present in the mixture of linear silicone oils in a content greater than or equal to 40% by weight relative to the total weight of the mixture of linear silicone oils, preferably greater than or equal to 45% by weight. They may each represent from 40% to 50% by weight, preferably from 45% to 50% by weight relative to the total weight of the mixture of linear silicone oils.

According to one embodiment, the composition comprises:
- at least one first linear silicone oil, preferably a polydimethylsiloxane, having a viscosity ranging from 100 to 400 $mm^2/s$, preferably from 200 to 380 $mm^2/s$, in particular of 350 $mm^2/s$,
- at least one second linear silicone oil, preferably a polydimethylsiloxane, having a viscosity ranging from 1 to 7 $mm^2/s$, preferably from 2 to 6 $mm^2/s$, in particular of 5 $mm^2/s$,
- at least one third linear silicone oil, preferably a polydimethylsiloxane, having a viscosity ranging from 8 to 20 $mm^2/s$, preferably from 8 to 15 $mm^2/s$, in particular of 10 $mm^2/s$.

According to one embodiment, the composition comprises:
- at least one first linear silicone oil, preferably a polydimethylsiloxane, having a viscosity ranging from 100 to 400 $mm^2/s$, preferably from 200 to 380 $mm^2/s$, in particular of 350 $mm^2/s$, in a content less than or equal to 20% by weight, preferably less than or equal to 10% by weight, relative to the total weight of the linear silicone oils,
- at least one second linear silicone oil, preferably a polydimethylsiloxane, having a viscosity ranging from 1 to 7 $mm^2/s$, preferably from 2 to 6 $mm^2/s$, in particular of 5 $mm^2/s$, in a content greater than or equal to 40% by weight, preferably greater than or equal to 45% by weight, relative to the total weight of the linear silicone oils,
- at least one third linear silicone oil, preferably a polydimethylsiloxane, having a viscosity ranging from 8 to 20 $mm^2/s$, preferably from 8 to 15 $mm^2/s$, in particular of 10 $mm^2/s$, in a content greater than or equal to 40% by weight, preferably greater than or equal to 45% by weight, relative to the total weight of the linear silicone oils.

According to one embodiment, the composition comprises:
- at least one first linear silicone oil, preferably a polydimethylsiloxane, having a viscosity ranging from 100 to 400 $mm^2/s$, preferably from 200 to 380 $mm^2/s$, in particular of 350 $mm^2/s$, in a content ranging from 0.5% to 15% by weight, preferably from 1% to 10% by weight, better still from 1% to 5% by weight relative to the total weight of the linear silicone oils,
- at least one second linear silicone oil, preferably a polydimethylsiloxane, having a viscosity ranging from 1 to 7 $mm^2/s$, preferably from 2 to 6 $mm^2/s$, in particular of 5 $mm^2/s$, in a content ranging from 40% to 50% by weight, preferably from 45% to 50% by weight, better still from 45% to 49.5% by weight relative to the total weight of the linear silicone oils,
- at least one third linear silicone oil, preferably a polydimethylsiloxane, having a viscosity ranging from 8 to 20 $mm^2/s$, preferably from 8 to 15 $mm^2/s$, in particular of 10 $mm^2/s$, in a content ranging from 40% to 55% by weight, preferably from 42% to 52% by weight, better still from 45% to 50% by weight relative to the total weight of the linear silicone oils.

As linear silicone oils that can be used in the composition according to the invention, mention may be made, for example, of the PDMSs DC 200 Fluid 5 cSt, 10 cSt and 350 cSt sold by the company Dow Corning or the one sold by the company Wacker under the name Wacker Belsil DM 10.

According to one variant of the invention, the composition according to the invention comprises at least one first linear silicone oil having a viscosity of less than 10 $mm^2/s$, preferably less than or equal to 7 $mm^2/s$, and more preferentially still of between 3 and 7 $mm^2/s$.

It also comprises at least one second linear silicone oil having a viscosity greater than or equal to 10 $mm^2/s$, preferably between 10 and 100 $mm^2/s$, preferentially between 10 and 50 $mm^2/s$, and more preferentially still between 10 and 30 $mm^2/s$.

According to this variant, the relative contents of each of these two oils are preferably such that one of the two oils is in an amount at least 1.5 times greater than the other.

The linear silicone oils may represent from 80% to 99% by weight, preferably from 85% to 98% by weight and better still from 90% to 95% by weight of the total weight of the mixture (linear silicone oils and silica aerogels).

The composition according to the invention may comprise the mixture (silicone oils and silica aerogel particles) in a content ranging from 0.1% to 90% by weight, preferably from 1% to 80% by weight, better still from 2% to 30% by weight, and even better still from 2% to 20% by weight, relative to the total weight of the composition.

The composition according to the invention may be aqueous or anhydrous.

The composition according to the invention may be in any galenic form conventionally used for a topical application and especially in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. It may also be in the form of hot-cast sticks or loose or compacted powders.

These compositions are prepared according to the usual methods.

According to one embodiment of the invention, the composition is in the form of an O/W emulsion or an aqueous gel.

The compositions of the invention may be used in any cosmetic or dermatological application, for example in cosmetics for caring for the skin, the hair, the scalp, the eyelashes, the eyebrows, the nails or mucous membranes (the lips), for example as protecting, treating or care products for the face, the hands or the body, as skin-cleansing products (for the face or the body), as makeup products (for example foundations) or as haircare products.

The composition according to the invention may comprise, besides the linear silicone oils of the mixture (silica aerogel particles and linear silicone oils), at least one "additional" oil.

As oils that can be used in the composition of the invention, examples that may be mentioned include:

- hydrocarbon-based oils of animal origin, such as perhydrosqualene (or squalane);
- hydrocarbon-based oils of plant origin, such as liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and the liquid fractions of shea butter;
- synthetic esters and ethers, especially of fatty acids or of fatty alcohols, for instance the oils of formulae $R^1COOR^2$ and $R^1OR^2$ in which $R^1$ represents a fatty acid residue containing from 8 to 29 carbon atoms and $R^2$ represents a branched or unbranched hydrocarbon-based chain containing from 3 to 30 carbon atoms, for instance purcellin oil, isononyl isononanoate, isopropyl myristate, 2-ethylhexyl palmitate (or octyl palmitate), 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alcohol heptanoates, octanoates and decanoates; polyol esters, for instance propylene glycol dioctanoate, neopentyl glycol diheptanoate and diethylene glycol diisononanoate; pentaerythritol esters, for instance pentaerythrityl tetraisostearate; and lipophilic amino acid derivatives, such as isopropyl lauroyl sarcosinate (INCI name: Isopropyl Lauroyl Sarcosinate) sold under the name Eldew SL 205 by the company Ajinomoto;
- linear or branched hydrocarbons, of mineral or synthetic origin, such as mineral oils (mixture of hydrocarbon-based oils derived from petroleum; INCI name: Mineral oil), volatile or non-volatile liquid paraffins, and derivatives thereof, petroleum jelly, polydecenes, isohexadecane, isododecane, hydrogenated isoparaffin for instance hydrogenated polyisobutene such as Parleam® oil sold by the company NOF Corporation (INCI name: Hydrogenated Polyisobutene);
- fatty alcohols containing from 8 to 26 carbon atoms, for instance cetyl alcohol, stearyl alcohol and mixtures thereof (cetylstearyl alcohol), octyldodecanol, 2-butyloctanol, 2-hexyldecanol, 2-undecylpentadecanol or oleyl alcohol;
- partially hydrocarbon-based and/or silicone-based fluoro oils, for instance those described in document JP-A-2-295 912;
- cyclic volatile silicone oils, for instance cyclopolydimethylsiloxanes (cyclomethicones) such as cyclopentasiloxane and cyclohexadimethylsiloxane; polydimethylsiloxanes comprising phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenyl-methyldiphenyltrisiloxanes and 2-phenylethyltrimethyl siloxysilicates, and polymethyl-phenylsiloxanes;

mixtures thereof.

The other fatty substances that may be present in the oily phase are, for example, fatty acids comprising from 8 to 30 carbon atoms, for instance stearic acid, lauric acid or palmitic acid; gums such as silicone gums (dimethiconol); silicone resins such as trifluoromethyl($C_{1-4}$)alkyl dimethicone and trifluoropropyl dimethicone; pastes such as petrolatum; waxes such as microcrystalline waxes, paraffin waxes, lignite waxes, ceresin, ozokerite, montan wax, beeswax, lanolin and derivatives thereof, candelilla wax, ouricurry wax, carnauba wax, Japan wax, cocoa butter, palm oil in paste form at 20° C., cork fibre wax, sugar cane wax, hydrogenated oils that are solid at 25° C., fatty esters and glycerides that are solid at 25° C., polyethylene waxes, the waxes obtained by Fischer-Tropsch synthesis, and silicone waxes; and mixtures of these fatty substances.

According to one embodiment, the composition according to the invention comprises less than 2% by weight and preferably less than 1% by weight of silicone elastomer solids, and better still is free of silicone elastomers. Silicone elastomers or elastomeric organopolysiloxanes. The term "elastomer" means a deformable, flexible solid material having viscoelastic properties and especially the consistency of a sponge or of a supple sphere. Its modulus of elasticity is such that this material withstands deformation and has limited stretchability and contractability. This material is capable of regaining its original shape after stretching. This elastomer is formed from chains of high molecular weight polymer, the mobility of which is limited by a uniform network of crosslinking points.

Elastomeric organopolysiloxanes are generally partially or completely crosslinked and may be in the form of particles.

Such elastomers are, for example, the products sold under the name KSG by the company Shin-Etsu, under the name Trefil by the company Dow Corning or under the name Gransil by the company Grant Industries.

The composition according to the invention may comprise an aqueous phase, the amount of which may range, for example, from 30% to 98% by weight, preferably from 40% to 98% by weight, better still from 50% to 98% by weight and even better still from 55% to 98% by weight relative to the total weight of the composition.

Conventionally, the aqueous phase may contain, besides water, one or more water-soluble solvents chosen from polyols (or polyhydric alcohols) and water-soluble lower alcohol(s), and mixtures thereof. The term "lower alcohol" means an alcohol comprising from 1 to 8 and preferably from 1 to 6 carbon atoms. Examples of lower alcohols that may be mentioned include ethanol, isopropanol and butanol, and mixtures thereof.

Examples of polyols that may be mentioned include glycerol; glycols such as propylene glycol or butylene glycol; sorbitol; sugars such as glucose, fructose, maltose, lactose and sucrose; and mixtures thereof.

The amount of water-soluble solvents (polyols and lower alcohols) may range, for example, from 0.5% to 30% by weight, preferably from 0.5% to 20% by weight and better still from 1% to 15% by weight relative to the total weight of the composition.

Adjuvants

In a known manner, the composition of the invention may also contain adjuvants that are common in cosmetics and/or dermatology, such as active agents, preserving agents, antioxidants, complexing agents, pH modifiers (acidic or basic), fragrances, fillers, bactericides, odour absorbers, colorants (pigments and dyes), film-forming polymers, emulsifiers such as fatty acid esters of polyethylene glycol, fatty acid esters of glycerol and fatty acid esters of sorbitan, which are optionally polyoxyethylenated, polyoxyethylenated fatty alcohols and fatty acid esters or ethers of sugars such as sucrose or glucose; thickeners and/or gelling agents, in particular polyacrylamides, acrylic homopolymers and copolymers, and acrylamidomethylpropanesulphonic acid homopolymers and copolymers, and also lipid vesicles. The amounts of these various adjuvants are those conventionally used in the field under consideration, for example from 0.01% to 20% of the total weight of the composition. Depending on their nature, these adjuvants may be introduced into the fatty phase, into the aqueous phase and/or into the lipid vesicles.

Needless to say, a person skilled in the art will take care to select this or these optional additional compound(s), and/or the amount thereof, such that the mattifying/soft focus properties of the composition according to the invention are not, or are not substantially, adversely affected by the envisaged addition.

In the patent application, unless specifically mentioned otherwise, the contents are expressed on a weight basis relative to the total weight of the composition.

The examples that follow are aimed at illustrating the compositions and processes according to this invention, but are not in any way a limitation of the scope of the invention. All the parts and percentages in the examples are given on a weight basis and all the measurements were obtained at about 25° C., unless otherwise mentioned.

EXAMPLES

Examples 1 to 5

5 compositions were prepared, comprising 7% of hydrophobic silica aerogel particles (VM-2270 from Dow Corning) and 93% of the following mixtures of linear silicone oils.

|  | Example 1 (invention) | Example 2 (invention) | Example 3 (comparative) | Example 4 (comparative) | Example 5 (comparative) |
| --- | --- | --- | --- | --- | --- |
| Dimethicone 350 cSt | 3.2 | 2 | 100 | — | — |
| Dimethicone 10 cSt | 45.7 | 49 | — | 100 | — |
| Dimethicone 5 cSt | 51.1 | 49 | — | — | 100 |
| Macroscopic appearance | gel that does not flow | gel that does not flow | non-homogeneous sample | gel that flows | gel that flows |
| Appearance after application to the skin | matt | matt | N/A | shiny | shiny |

The compositions are obtained by introducing the silica aerogel particles with gentle paddle stirring.

These compositions were evaluated visually by three individuals who then applied each composition to the back of the hand and marked them as matt/shiny in comparison with bare skin.

Only the compositions comprising the mixtures from Examples 1 and 2 according to the invention are in the form of a gel which does not flow and which, when applied to the skin, is characterized by a matt, soft-focus deposit.

Example 6: Cream for Oily Skins

| Phase | INCI name | |
| --- | --- | --- |
| A | WATER | qs 100 |
|  | GLYCEROL | 5.00 |
|  | DISODIUM EDTA | 0.05 |
|  | PROPYLENE GLYCOL | 6.60 |
| B | CAPRYLYL GLYCOL | 0.15 |
|  | ISOHEXADECANE | 3.50 |
|  | POLYSORBATE 80 (TWEEN 80-LQ-(WL) from Croda) | 1.00 |
|  | DIMETHICONE (and) CETETH-10 (and) LAURETH-4 (DOW CORNING 7-3099 DIMETHICONE HIP EMULSION) | 1.50 |
|  | DIMETHICONE 350 cSt | 0.3 |
|  | DIMETHICONE 10 cSt | 4.25 |
|  | DIMETHICONE 5 cSt | 4.75 |
| C | ISOHEXADECANE | 2.00 |
|  | CARBOMER (CARBOPOL 981 from Lubrizol) | 0.15 |
| D | SODIUM HYDROXIDE | 0.06 |
|  | WATER | 0.54 |
|  | AMMONIUM POLYACRYLOYLDIMETHYL TAURATE (Hostacerin AMPS from Clariant) | 1.80 |
| E | NYLON-12 (ORGASOL 2002 EXD NAT COS from Arkema) | 0.50 |
|  | Ethanol | 5.00 |
| G | Hydrophobic silica aerogel particles (VM-2270 from Dow Corning) | 0.7 |

Procedure:

heat phase B to around 70° C.;

heat phase A to around 70° C.;

produce the emulsion by incorporating phase A into phase B;

at 40-45° C. incorporate the remaining phases and continue stirring until cooling is complete.

Example 7: Moisturizing Cream

| Phase | INCI name | |
| --- | --- | --- |
| A1 | WATER | qs 100 |
|  | BUTYLENE GLYCOL | 5.00 |
|  | GLYCEROL | 5.00 |
|  | TETRASODIUM EDTA | 0.20 |
|  | PHENOXYETHANOL | 0.70 |
| B | GLYCERYL STEARATE (and) PEG-100 STEARATE (ARLACEL 165-FL from Croda) | 2.00 |
|  | CETYL ALCOHOL | 0.50 |
|  | METHYLPARABEN | 0.25 |
|  | PEG-20 STEARATE (MYRJ S20-PA-(WL) from Croda) | 0.80 |
|  | STEARYL ALCOHOL | 0.50 |
|  | STEARIC ACID | 3.00 |
|  | CAPRYLOYL SALICYLIC ACID (MEXORYL SAB from Chimex) | 0.05 |
|  | AMMONIUM POLYACRYLOYLDIMETHYL TAURATE (Hostacerin AMPS from Clariant) | 1.60 |
|  | DIMETHICONE 350 cSt | 0.15 |
|  | DIMETHICONE 10 cSt | 3.64 |
|  | DIMETHICONE 5 cSt | 3.64 |
| B2 | TRIETHANOLAMINE | 0.30 |
| B3 | Hydrophobic silica aerogel particles (VM-2270 from Dow Corning) | 0.56 |

Procedure:

heat phase B to around 75° C.;

heat phase A to around 75° C.;

produce the emulsion by incorporating phase A into phase B;

at 40-45° C. incorporate the remaining phases and continue stirring until cooling is complete.

The creams from Examples 6 and 7 are comfortable and soft on application, and make it possible to obtain a good mattifying effect on the skin.

Example 8

The following mixtures were produced:

| Mixture | 1 (invention) | 2 (comparative) | 3 (invention) | 4 (comparative) |
|---|---|---|---|---|
| Polydimethyl-siloxane 350 cSt | 1.86 | — | — | — |
| Polydimethyl-siloxane 10 cSt | 45.5 | 93 | 23.25 | — |
| Polydimethyl-siloxane 5 cSt | 45.5 | — | 69.75 | 93 |
| Silica aerogel | 7 | 7 | 7 | 7 |

By visually observing the appearance of the deposit obtained on the hand, it is observed that mixtures 1 and 3 make it possible to mattify the skin and to smooth the microrelief of the skin.

There is therefore clearly an effect of correcting skin imperfections which is not possible with comparative mixtures 2 and 4.

The invention claimed is:

1. A cosmetic composition, comprising:
hydrophobic silica aerogel particles having a specific surface area per unit of mass ($S_M$) ranging from 500 to 1500 m$^2$/g and a size expressed as a volume-average diameter (D[0.5]) ranging from 1 to 1500 µm; and
at least one first linear silicone oil having a viscosity greater than 50 mm$^2$/s and at least second and third linear silicone oils each having a viscosity less than or equal to 50 mm$^2$/s.

2. The composition according to claim 1, wherein the first linear silicone oil has a viscosity from 100 mm$^2$/s to 1000 mm$^2$/s.

3. The composition according to claim 1, wherein the second and third linear silicone oils each has a viscosity less than or equal to 30 mm$^2$/s.

4. The composition of claim 1, wherein the first linear silicone oil is present in a content less than or equal to 20% by weight relative to the total weight of the linear silicone oils present.

5. The composition of claim 1, wherein the second and third linear silicone oil is each present in a content greater than or equal to 40% by weight relative to the total weight of the linear silicone oils present.

6. The composition of claim 1, comprising:
at least one first linear silicone oil having a viscosity ranging from 100 to 400 mm$^2$/s,
at least one second linear silicone oil having a viscosity ranging from 1 to 7 mm$^2$/s, and
at least one third linear silicone oil having a viscosity ranging from 8 to 20 mm$^2$/s.

7. The composition of claim 1, comprising:
at least one first linear silicone oil having a viscosity ranging from 100 to 400 mm$^2$/s, in a content less than or equal to 20% by weight, relative to the total weight of the linear silicone oils,
at least one second linear silicone oil having a viscosity ranging from 1 to 7 mm$^2$/s, in a content greater than or equal to 40% by weight, relative to the total weight of the linear silicone oils, and
at least one third linear silicone oil having a viscosity ranging from 8 to 20 mm$^2$/s, in a content greater than or equal to 40% by weight, relative to the total weight of the linear silicone oils.

8. The composition of claim 1, comprising:
at least one first linear silicone oil having a viscosity ranging from 100 to 400 mm$^2$/s, in a content ranging from 0.5% to 15% by weight relative to the total weight of the linear silicone oils,
at least one second linear silicone oil having a viscosity ranging from 1 to 7 mm$^2$/s, in a content ranging from 40% to 50% by weight relative to the total weight of the linear silicone oils, and
at least one third linear silicone oil having a viscosity ranging from 8 to 20 mm$^2$/s, in a content ranging from 40% to 55% by weight, relative to the total weight of the linear silicone oils.

9. A cosmetic composition, comprising:
hydrophobic silica aerogel particles having a specific surface area per unit of mass ($S_M$) ranging from 500 to 1500 m$^2$/g and a size expressed as a volume-average diameter (D[0.5]) ranging from 1 to 1500 µm, and
at least one first linear silicone oil having a viscosity less than 10 mm$^2$/s, and at least one second linear silicone oil having a viscosity greater than or equal to 10 mm$^2$/s;
wherein the composition does not contain a linear fluorine-modified silicone oil.

10. The composition according to claim 2 with the exception of the following compositions:

| Composition | a | b |
|---|---|---|
| Dimethicone 350 cSt | 2.976 | 1.86 |
| Dimethicone 10 cSt | 42.501 | 45.57 |
| Dimethicone 5 cSt | 47.523 | 45.57 |
| Silica aerogel (VM-2270 from Dow Corning) | 7 | 7 |

| | Composition c | |
|---|---|---|
| Phase | INCI name | |
| A | WATER | qs 100 |
| | GLYCEROL | 5.00 |
| | DISODIUM EDTA | 0.05 |
| | PROPYLENE GLYCOL | 6.60 |
| B | CAPRYLYL GLYCOL | 0.15 |
| | ISOHEXADECANE | 3.50 |
| | POLYSORBATE 80 (TWEEN 80-LQ-(WL) from Croda) | 1.00 |
| | DIMETHICONE (and) CETETH-10 (and) LAURETH-4 (DOW CORNING 7-3099 DIMETHICONE HIP EMULSION) | 1.50 |
| | Dimethicone 350 cSt | 0.3 |
| | Dimethicone 10 cSt | 4.25 |
| | Dimethicone 5 cSt | 4.75 |
| C | ISOHEXADECANE | 2.00 |
| | CARBOMER (CARBOPOL 981 from Lubrizol) | 0.15 |
| D | SODIUM HYDROXIDE | 0.06 |
| | WATER | 0.54 |
| | AMMONIUM POLYACRYLOYLDIMETHYL TAURATE (Hostacerin AMPS from Clariant) | 1.80 |

-continued

Composition c

| Phase | INCI name | |
|---|---|---|
| E | NYLON-12 (ORGASOL 2002 EXD NAT COS from Arkema) | 0.50 |
| | Ethanol | 5.00 |
| G | Hydrophobic silica aerogel particles (VM-2270 from Dow Corning) | 0.7 |

Composition d

| Phase | INCI name | |
|---|---|---|
| A1 | WATER | qs 100 |
| | BUTYLENE GLYCOL | 5.00 |
| | GLYCEROL | 5.00 |
| | TETRASODIUM EDTA | 0.20 |
| | PHENOXYETHANOL | 0.70 |
| B | GLYCERYL STEARATE (and) PEG-100 STEARATE (ARLACEL 165-FL from Croda) | 2.00 |
| | CETYL ALCOHOL | 0.50 |
| | METHYLPARABEN | 0.25 |
| | PEG-20 STEARATE (MYRJ S20-PA-(WL) from Croda) | 0.80 |
| | STEARYL ALCOHOL | 0.50 |
| | STEARIC ACID | 3.00 |
| | CAPRYLOYL SALICYLIC ACID (MEXORYL SAB from Chimex) | 0.05 |
| | AMMONIUM POLYACRYLOYLDIMETHYL TAURATE (Hostacerin AMPS from Clariant) | 1.60 |
| | Dimethicone 350 cSt | 0.15 |
| | Dimethicone 10 cSt | 3.64 |
| | Dimethicone 5 cSt | 3.64 |
| B2 | TRIETHANOLAMINE | 0.30 |
| B3 | Hydrophobic silica aerogel particles (VM-2270 from Dow Corning). | 0.56 |

11. The composition of claim 9, wherein the relative contents of each of the two oils is such that one of the two oils is in an amount at least 1.5 times greater than the other.

12. The composition of claim 1, wherein the hydrophobic silica aerogel particles have a specific surface area per unit of mass ranging from 600 to 1200 m²/g.

13. The composition of claim 1, wherein the hydrophobic silica aerogel particles have a size expressed as the volume-average diameter ranging from 1 to 1000 μm.

14. The composition of claim 1, wherein the hydrophobic silica aerogel particles have a specific surface area per unit of mass ($S_M$) ranging from 600 to 800 m²/g and a size expressed as the volume-average diameter (D[0.5]) ranging from 5 to 20 μm.

15. The composition of claim 1, wherein the hydrophobic silica aerogel particles have a tapped density ranging from 0.04 g/cm³ to 0.10 g/cm³.

16. The composition of claim 1, wherein the hydrophobic silica aerogel particles have a specific surface area per unit of volume $S_V$ ranging from 5 to 60 m²/cm³.

17. The composition of claim 1, wherein the hydrophobic silica aerogel particles have an oil absorption capacity, measured at the wet point, ranging from 5 to 18 ml/g.

18. The composition of claim 1, wherein the hydrophobic silica aerogel particles are trimethylsiloxyl silica particles.

19. The composition of claim 1, wherein the silica aerogel particles represent from 0.5% to 30% by weight of the total amount of linear silicone oils and silica aerogel particles present.

20. The composition of claim 1, wherein the silicone oils represent from 80% to 99% by weight of the total weight of total amount of linear silicone oils and silica aerogel particles present.

21. The composition of claim 1, wherein the linear silicone oils are polyorganosiloxanes comprising alkylsiloxane repeat units.

22. The composition of claim 1, wherein the linear silicone oils are polydimethylsiloxanes.

23. The composition of claim 1, comprising from 0.1% to 90% by weight of the total amount of linear silicone oils and silica aerogel particles present.

24. A cosmetic method for making up and/or caring for a keratin material, the method comprising applying the composition of claim 1 to said material.

* * * * *